(12) United States Patent
Mazzocchi et al.

(10) Patent No.: US 7,787,934 B2
(45) Date of Patent: Aug. 31, 2010

(54) FIDUCIAL MARKER DEVICES, TOOLS, AND METHODS

(75) Inventors: Rudy A. Mazzocchi, Indian Harbor Beach, FL (US); Matthew S. Solar, Indialantic, FL (US); David M. Lee, Melbourne Beach, FL (US)

(73) Assignee: Medtronic, Inc., Minneapolis, MN (US)

( * ) Notice: Subject to any disclaimer, the term of this patent is extended or adjusted under 35 U.S.C. 154(b) by 1660 days.

(21) Appl. No.: 10/454,145

(22) Filed: Jun. 4, 2003

(65) Prior Publication Data

US 2004/0030236 A1 Feb. 12, 2004

Related U.S. Application Data

(63) Continuation-in-part of application No. 10/206,884, filed on Jul. 29, 2002, now abandoned.

(51) Int. Cl.
*A61B 5/00* (2006.01)

(52) U.S. Cl. ........................ 600/426; 600/414

(58) Field of Classification Search ................ 600/414, 600/426, 431; 606/76, 301, 302, 304, 305, 606/308–311, 315, 318, 321, 322; 378/20, 378/163, 204, 205
See application file for complete search history.

(56) References Cited

U.S. PATENT DOCUMENTS

| | | |
|---|---|---|
| 2,650,588 A | 9/1953 | Radcliffe |
| 4,228,799 A | 10/1980 | Anichkov et al. |
| 4,408,372 A | 10/1983 | Kimura et al. |
| D274,117 S | 6/1984 | Lapps |
| 4,583,538 A | 4/1986 | Onik et al. |
| 4,629,451 A | 12/1986 | Winters et al. |
| 4,630,375 A | 12/1986 | Spolyar |
| 4,675,173 A | 6/1987 | Widder |
| 4,763,548 A | 8/1988 | Leibinger et al. |
| D306,190 S | 2/1990 | Poulsen |
| 4,931,056 A | 6/1990 | Ghajar et al. |
| 4,943,293 A | 7/1990 | Lee, Jr. |
| 4,943,298 A | 7/1990 | Fujita et al. |

(Continued)

FOREIGN PATENT DOCUMENTS

DE 9112356 2/1992

(Continued)

OTHER PUBLICATIONS

"Bone Anchor", U.S. Appl. No. 10/405,881, filed Apr. 2, 2003.

(Continued)

*Primary Examiner*—Ruth S Smith
(74) *Attorney, Agent, or Firm*—Harness, Dickey & Pierce, PLC

(57) ABSTRACT

This document discusses, among other things, a fiducial marker assembly that includes an internally engagable base. The base is sized and shaped to be mounted flush to or recessed from an outer surface of a patient's skull, thereby reducing or avoiding patient discomfort. The fiducial marker assembly includes an imagable locator and a registration receptacle. A base insertion instrument is engaged to the base to attach the base to the patient's skull. In one example the base includes a faceted head, permitting a socket-like device to screw or unscrew the base into or out of the skull. In another example, the base includes at least one step or slot for engaging an insertion or extraction tool.

25 Claims, 12 Drawing Sheets

U.S. PATENT DOCUMENTS

| | | | |
|---|---|---|---|
| 4,945,914 A | 8/1990 | Allen | 128/653 R |
| 4,954,914 A | 9/1990 | Karita et al. | |
| 4,991,579 A | 2/1991 | Allen | |
| 5,016,639 A | 5/1991 | Allen | 128/653 R |
| 5,042,462 A | 8/1991 | Bremer | |
| 5,058,580 A | 10/1991 | Hazard | |
| 5,094,241 A | 3/1992 | Allen | 128/653.1 |
| 5,098,435 A | 3/1992 | Stednitz et al. | |
| 5,119,817 A | 6/1992 | Allen | 128/653.1 |
| 5,142,930 A | 9/1992 | Allen et al. | |
| 5,178,164 A | 1/1993 | Allen | 128/898 |
| 5,186,174 A | 2/1993 | Schlondorff et al. | |
| 5,197,476 A | 3/1993 | Nowacki et al. | |
| 5,201,737 A | 4/1993 | Leibinger et al. | |
| 5,211,164 A | 5/1993 | Allen | |
| 5,222,499 A | 6/1993 | Allen et al. | |
| 5,230,338 A | 7/1993 | Allen et al. | |
| 5,263,980 A | 11/1993 | Leibinger et al. | |
| 5,299,253 A | 3/1994 | Wessels | 378/163 |
| 5,300,075 A | 4/1994 | Gordon | |
| 5,300,076 A | 4/1994 | Leriche | |
| 5,305,203 A | 4/1994 | Raab | |
| 5,368,030 A | 11/1994 | Zinreich et al. | |
| 5,383,454 A | 1/1995 | Bucholz | |
| 5,389,101 A | 2/1995 | Heilbrun et al. | 606/130 |
| 5,394,457 A | 2/1995 | Leibinger et al. | 378/162 |
| 5,394,875 A | 3/1995 | Lewis et al. | 128/660.09 |
| 5,397,329 A | 3/1995 | Allen | 606/73 |
| 5,417,692 A | 5/1995 | Goble et al. | |
| 5,468,242 A | 11/1995 | Reisberg et al. | |
| 5,469,847 A | 11/1995 | Zinreich et al. | |
| 5,494,034 A | 2/1996 | Schlondorff et al. | |
| 5,551,429 A | 9/1996 | Fitzpatrick et al. | 128/653.1 |
| 5,566,081 A | 10/1996 | Yoshizawa et al. | |
| 5,575,794 A | 11/1996 | Walus et al. | 606/116 |
| 5,590,215 A | 12/1996 | Allen | |
| 5,595,193 A | 1/1997 | Walus et al. | 128/898 |
| 5,603,318 A | 2/1997 | Heilbrun et al. | 128/630 |
| 5,636,255 A | 6/1997 | Ellis et al. | |
| 5,681,313 A | 10/1997 | Diez et al. | |
| 5,683,217 A | 11/1997 | Walther et al. | |
| 5,730,130 A | 3/1998 | Fitzpatrick et al. | 128/653.1 |
| 5,743,899 A | 4/1998 | Zinreich | 606/1 |
| 5,769,789 A | 6/1998 | Wang et al. | 600/414 |
| 5,799,099 A | 8/1998 | Wang et al. | 382/131 |
| 5,807,252 A | 9/1998 | Hassfeld et al. | |
| 5,807,396 A | 9/1998 | Raveh | |
| 5,836,954 A | 11/1998 | Heilbrun et al. | 606/130 |
| 5,851,183 A | 12/1998 | Bucholz | |
| 5,860,389 A * | 1/1999 | Caldwell | 119/28.5 |
| 5,871,445 A | 2/1999 | Bucholz | |
| 5,891,034 A | 4/1999 | Bucholz | |
| 5,916,164 A | 6/1999 | Fitzpatrick et al. | 600/426 |
| 5,954,722 A * | 9/1999 | Bono | 606/281 |
| 5,957,934 A | 9/1999 | Rapoport et al. | |
| 5,968,047 A | 10/1999 | Reed | |
| 5,984,930 A | 11/1999 | Maciunas et al. | |
| 6,000,892 A | 12/1999 | Takasaki et al. | |
| 6,006,126 A | 12/1999 | Cosman | |
| 6,011,987 A | 1/2000 | Barnett | 600/414 |
| 6,019,776 A | 2/2000 | Preissman et al. | |
| 6,052,477 A | 4/2000 | Wang et al. | 382/131 |
| 6,071,291 A | 6/2000 | Forst et al. | |
| 6,073,044 A | 6/2000 | Fitzpatrick et al. | 600/426 |
| 6,076,008 A | 6/2000 | Bucholz | |
| 6,082,366 A | 7/2000 | Andra et al. | |
| 6,096,048 A | 8/2000 | Howard, III et al. | 606/130 |
| 6,102,914 A | 8/2000 | Bulstra et al. | |
| 6,146,390 A | 11/2000 | Heilbrun et al. | 606/130 |
| 6,165,181 A | 12/2000 | Heilbrun et al. | 606/130 |
| 6,167,295 A | 12/2000 | Cosman | 600/426 |
| 6,168,780 B1 | 1/2001 | Andra | |
| 6,181,960 B1 | 1/2001 | Jensen et al. | 600/431 |
| 6,187,018 B1 | 2/2001 | Sanjay-Gopal et al. | 606/130 |
| 6,206,890 B1 | 3/2001 | Truwit | 606/130 |
| 6,226,548 B1 | 5/2001 | Foley et al. | |
| 6,236,875 B1 | 5/2001 | Bucholz et al. | |
| RE37,249 E | 6/2001 | Leibinger et al. | |
| 6,241,732 B1 | 6/2001 | Overaker et al. | |
| 6,261,300 B1 | 7/2001 | Carol et al. | |
| 6,273,896 B1 | 8/2001 | Franck et al. | 606/130 |
| 6,282,437 B1 | 8/2001 | Franck et al. | 600/429 |
| 6,298,262 B1 | 10/2001 | Franck et al. | 600/426 |
| 6,304,768 B1 | 10/2001 | Blume et al. | 600/407 |
| 6,306,126 B1 | 10/2001 | Moctezuma et al. | |
| 6,327,491 B1 | 12/2001 | Franklin et al. | |
| 6,333,971 B2 | 12/2001 | McCrory et al. | 378/162 |
| 6,351,659 B1 | 2/2002 | Vilsmeier et al. | |
| 6,351,662 B1 | 2/2002 | Franck et al. | 600/429 |
| 6,381,485 B1 | 4/2002 | Hunter et al. | 600/407 |
| 6,382,815 B1 | 5/2002 | Klearman et al. | |
| 6,402,757 B1 | 6/2002 | Moore, III et al. | |
| 6,405,072 B1 | 6/2002 | Cosman | |
| 6,419,680 B1 | 7/2002 | Cosman et al. | |
| 6,430,434 B1 | 8/2002 | Mittelstadt | |
| 6,454,769 B2 * | 9/2002 | Wagner et al. | 606/279 |
| 6,459,927 B1 | 10/2002 | Franklin et al. | |
| 6,464,706 B1 | 10/2002 | Winters | |
| 6,499,488 B1 | 12/2002 | Hunter et al. | |
| 6,546,277 B1 | 4/2003 | Franck et al. | |
| 6,565,573 B1 | 5/2003 | Ferrante et al. | |
| 6,694,168 B2 | 2/2004 | Traxel et al. | |
| 6,738,657 B1 | 5/2004 | Franklin et al. | |
| D493,198 S | 7/2004 | Starkel | |
| 6,865,907 B2 | 3/2005 | Andrews et al. | |
| 6,866,666 B1 | 3/2005 | Sinnott et al. | |
| 6,942,667 B1 | 9/2005 | Song | |
| RE39,133 E | 6/2006 | Clayton et al. | |
| D527,820 S | 9/2006 | Solar et al. | |
| D528,211 S | 9/2006 | Solar et al. | |
| 2001/0000186 A1 | 4/2001 | Bramlet et al. | |
| 2001/0004395 A1 | 6/2001 | McCrory et al. | 378/162 |
| 2001/0010004 A1 | 7/2001 | Traxel et al. | |
| 2001/0027271 A1 | 10/2001 | Franck et al. | |
| 2001/0051807 A1 | 12/2001 | Grafton | |
| 2002/0028423 A1 | 3/2002 | Levisman | |
| 2002/0052610 A1 | 5/2002 | Skakoon et al. | |
| 2002/0087101 A1 | 7/2002 | Barrick et al. | |
| 2002/0156363 A1 | 10/2002 | Hunter et al. | 600/410 |
| 2003/0040753 A1 | 2/2003 | Daum et al. | |
| 2003/0187351 A1 | 10/2003 | Franck et al. | |
| 2004/0019265 A1 | 1/2004 | Mazzocchi | |
| 2004/0019365 A1 | 1/2004 | Ding et al. | |
| 2004/0030236 A1 | 2/2004 | Mazzocchi et al. | |
| 2004/0030237 A1 | 2/2004 | Lee et al. | |
| 2004/0078084 A1 | 4/2004 | Albertorio | |
| 2004/0122305 A1 | 6/2004 | Grimm et al. | |
| 2004/0167391 A1 | 8/2004 | Solar et al. | |
| 2004/0167393 A1 | 8/2004 | Solar et al. | |
| 2004/0254581 A1 | 12/2004 | Leclair | |
| 2005/0015032 A1 | 1/2005 | Stein | |
| 2005/0042574 A1 | 2/2005 | Lazarof | |
| 2005/0043735 A1 | 2/2005 | Ahmad | |
| 2007/0225599 A1 | 9/2007 | Solar et al. | |

FOREIGN PATENT DOCUMENTS

| | | |
|---|---|---|
| EP | 0787467 | 8/1997 |
| EP | 0813846 | 12/1997 |
| EP | 0820736 | 1/1998 |
| EP | 1033113 | 9/2000 |
| EP | 1249207 | 10/2002 |
| RU | 2026648 | 1/1995 |
| WO | WO-9709929 | 3/1997 |

| | | |
|---|---|---|
| WO | WO-9838908 | 9/1998 |
| WO | WO-9911998 | 3/1999 |
| WO | WO 9916352 | 4/1999 |
| WO | WO-9940869 | 8/1999 |
| WO | WO-01/49197 | 7/2001 |
| WO | WO-0178015 | 10/2001 |
| WO | WO-200475768 | 10/2004 |

OTHER PUBLICATIONS

Leibinger, et al., "Microsurgical Neurectomy Bayonet Scissors", *The Leibinger Family of Neurosurgical Products*, (1993), 1 pg.

Leibinger, et al., "The ZD Stereotactic System", *Leibinger et al. v. McCrory et al.*, Interference No. 103,657, (1992), 19 pgs.

Office Action in U.S. Appl. No. 10/374,677 by James Kish, mailed Sep. 5, 2007.

Solar, M. S., et al., "Fiducial Marker", U.S. Appl. No. 29/199,266, filed Feb. 12, 2004 (723.079US1), 17 pgs.

"Acustar", *Z-KAT, Inc.*, http://www.z-kat.com/acustar.htm,(2002),5 pages, (viewed web site on Aug. 7, 2002).

"Multi-Modality Radiographic Markers", *IZI Medical Products*, http://www.izimed.com,(2002),pp. 1-12, (viewed web site on Aug. 7, 2002).

"Stryker Navigation System, The Smarter Vision—Image Guided Surgery", *Stryker Leibinger Inc.*, (2002),8 pages.

Clarysse, P, et al., "A Computer-Assisted System for 3-D Frameless Localization in Stereotaxic MRI", *IEEE Transactions on Medical Imaging*, 10, (1991),523-529.

Coste, E, et al., "Frameless Method of Stereotaxic Localization with DSA", *Radiology*, (1993),829-834.

Leibinger, et al., "The Leibinger™ Family of Neurosurgical Products", *Leibinger et al. v. McCrory et al.*, Interference No. 103,657,(1993),1.

Leibinger, et al., "The F.L. Fischer™ Stereotactic Products by Leibinger", *Leibinger et al. v. McCrory et al.*, Interference No. 103,657,(1993),1.

Leibinger, et al., "The ZD Stereotactic System", *Leibinger et al. v. McCrory et al.*, Interference No. 103,657,(1992),19.

Motti, E D., et al., "Head-holder inferfacing computed tomography with Talairach stereotactic frame", *Journal of Neurosurgical Sciences*, 27(3), (1983),219-223.

Rousseau, J., et al., "A frameless method for 3D MRI and CT guided stereotaxic localisation", *European Radiology* (1992),pp. 1286-1292.

Rousseau, et al., "Validation of a New Method for Stereotactic Localization Using MR Imaging", *Journal of Computer Assisted Tomography*, (1991),291-296.

Waltregny, et al., "Application of the Talairach stereotaxic system for the purpose of establishing a common reference plane for brain imaging techniques (CAT scan, NMRI, PET scan)", *Revue d Electroencephalographic et de Neuro-physiologie Clinique*, 16(3), (1986),269-271.

Leibinger, "Summary of Safety and Effectiveness", *Marker System for Stereotaxic Navigation*, (Mar. 1996),pp. 38-46.

* cited by examiner

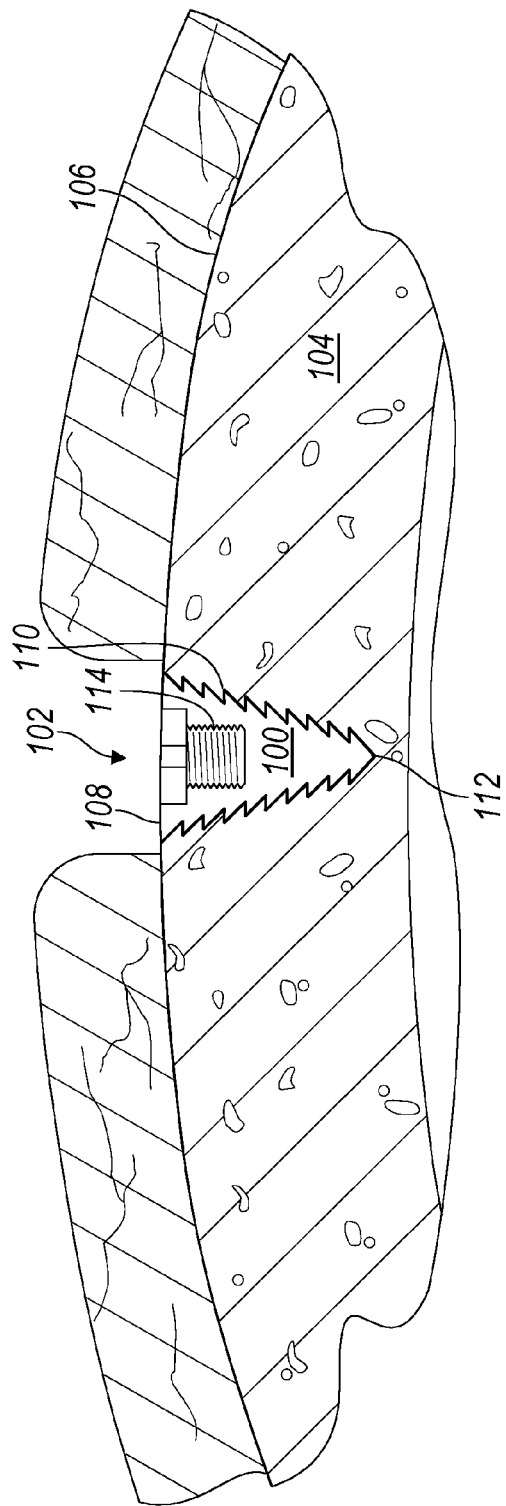
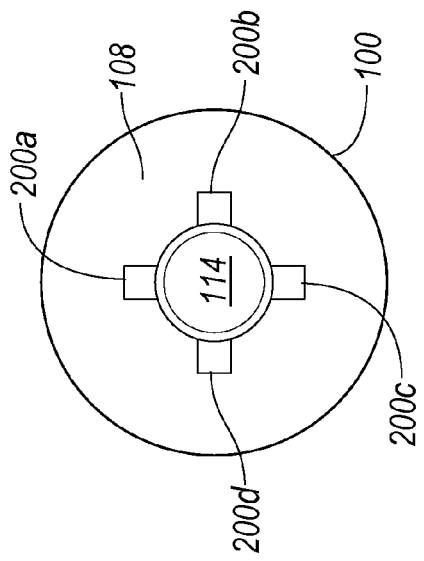
FIG. 1
FIG. 2

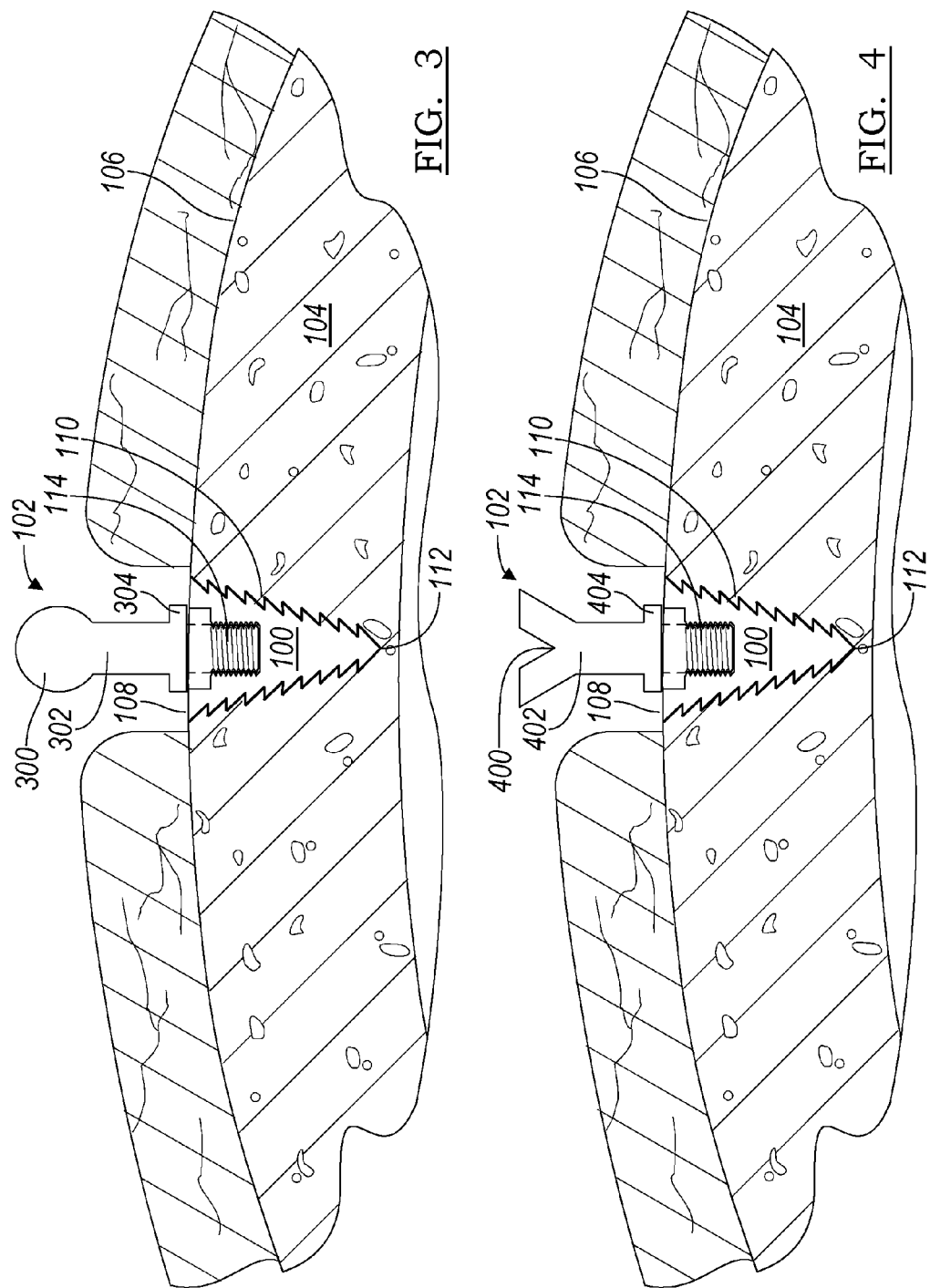

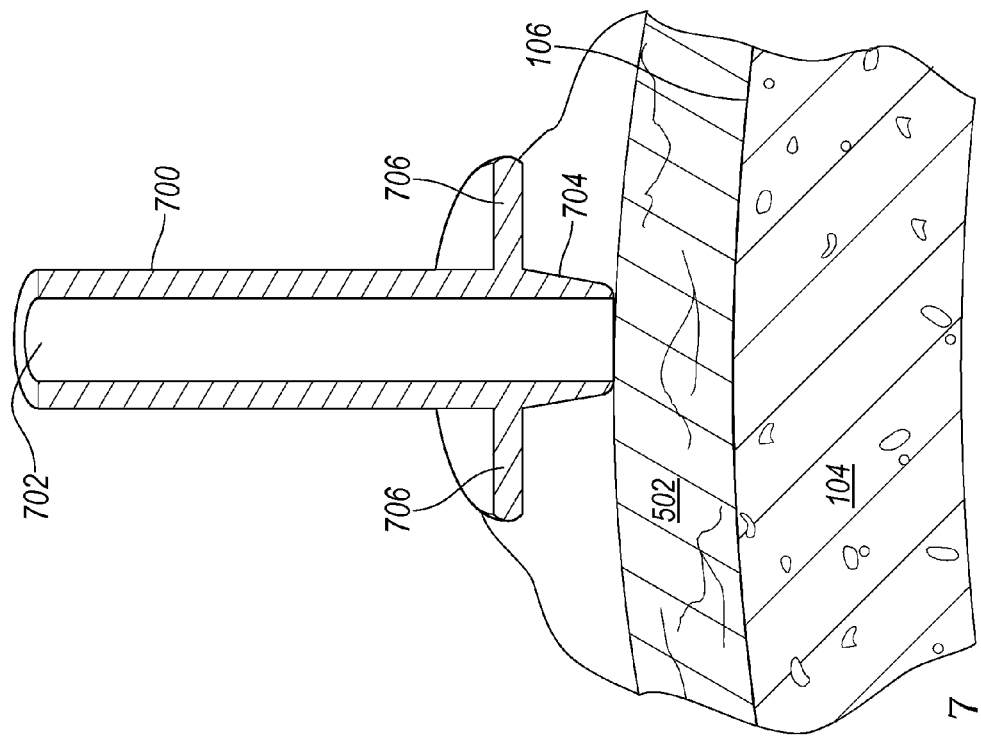
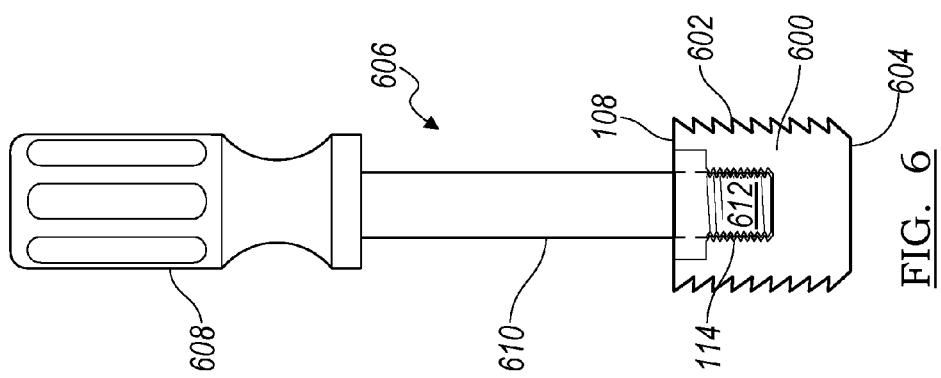

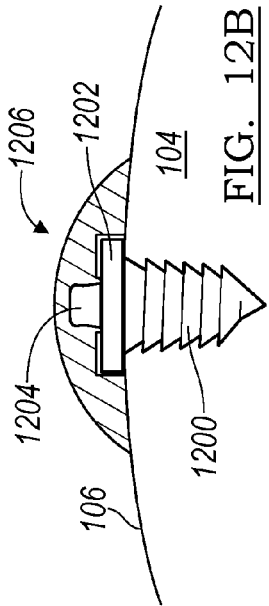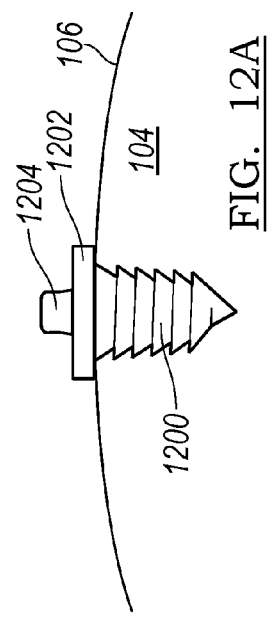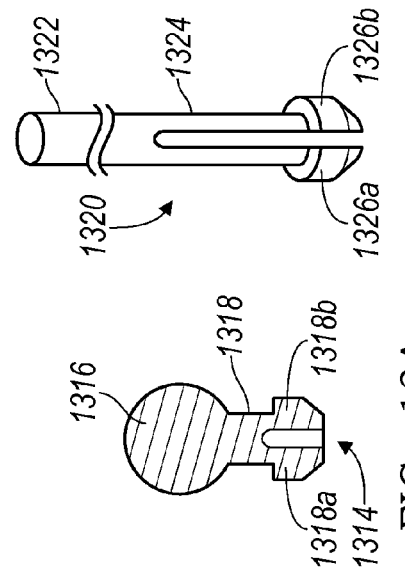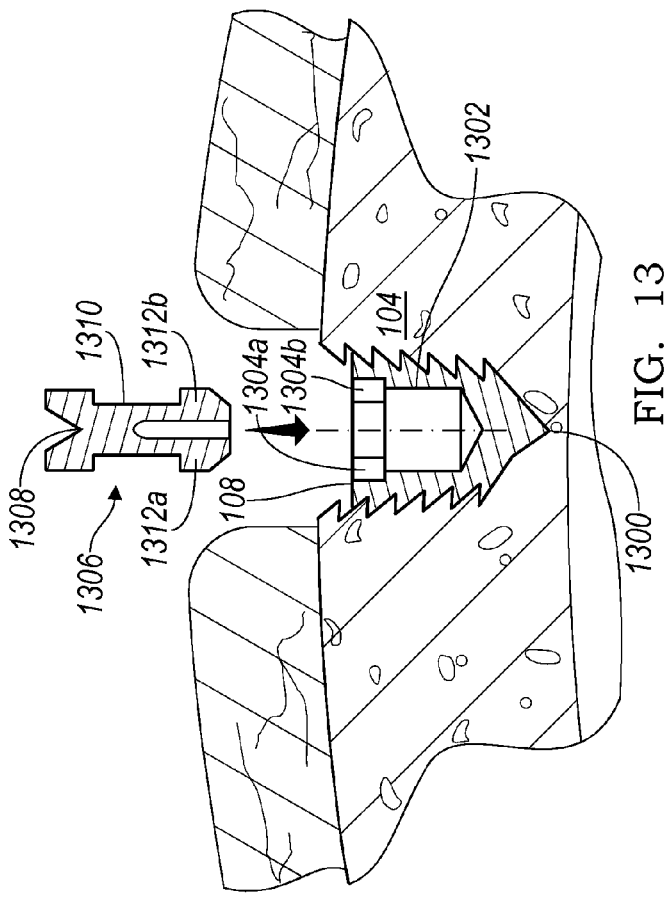

FIDUCIAL MARKER DEVICES, TOOLS, AND METHODS

CROSS-REFERENCE TO RELATED APPLICATION

This patent application is a continuation-in-part of Mazzocchi et al. U.S. patent application Ser. No. 10/206,884, entitled "FIDUCIAL MARKER DEVICES, TOOLS, AND METHODS", filed on Jul. 29, 2002, now abandoned which is incorporated herein by reference in its entirety.

This patent application is also related to Solar et al. U.S. patent application Ser. No. 10/374,677, entitled "FIDUCIAL MARKER DEVICES, TOOLS, AND METHODS," filed on Feb. 25, 2003, which is incorporated herein by reference in its entirety.

This patent application is also related to Lee et al. U.S. patent application Ser. No. 10/454,786, entitled "FIDUCIAL MARKER DEVICES AND METHODS," filed on (Jun. 4, 2003) even date herewith which is incorporated herein by reference in its entirety.

FIELD OF THE INVENTION

This document relates generally to imaging a patient for performing surgical intervention, and more specifically, but not by way of limitation, to fiducial marker devices and associated tools and methods.

BACKGROUND

Fiducial markers that can be located and recognized by an imaging system are useful in neurosurgery and other applications. For example, in one technique, multiple fiducial markers are screwed into the patient's skull to define recognizable landmarks that appear on a preoperative image of the patient's brain. Such a bone-anchored fiducial marker typically includes an externally threaded bone-screw portion, which is driven into the skull, and a threaded shaft that rises up and out of the skull from the bone-screw. The threaded shaft typically receives a screwed-on imagable sphere that is visible on a magnetic resonance imaging (MRI) image or computed tomography (CT) image. The multiple fiducial markers on the patient's skull define landmarks on preoperative images that are useful to the physician for planning entry coordinates and a trajectory to a target location in the brain. An image-guided workstation uses these preoperative images and planning to guide the neurosurgeon while actually performing the subsequent surgical procedure.

After the preoperative planning phase, the patient is brought into the operating room so that the planned surgical procedure can be performed. On the operating table, the patient's skull is clamped in a head-frame or otherwise immobilized. In order to use the preoperative images provided by the image-guided workstation to guide the surgeon during the procedure, the patient's skull must first be "registered" to the preoperative images. The registration creates an association between (1) the actual physical location of the fiducial markers on the patient's skull in the operating room and (2) the locations of the images of the fiducial markers visible on the preoperatively-obtained images.

According to one registration technique, a "wand" is used to perform the registration. The wand includes multiple light-emitting diode (LED) locators or reflective locators, which are visible to an infrared or other camera in the operating room. The camera is connected to the image-guided workstation. The locators define the position of the wand in the operating room, including the position of a sharp tip portion of the wand, which is in a known physical relationship to the locators. To register the patient, the imagable spheres are unscrewed from the fiducial marker shafts, and replaced by respective "divots" that are sized and shaped to receive the wand tip. These divots are screwed onto the fiducial marker shafts, such that the maximum depression point of the tip corresponds to the same location as the center of the imagable sphere when the imagable sphere was screwed onto the fiducial marker shaft. A reference divot is also present in the operating room at a known location, such as on the operating table or head-frame. During the patient registration process, the surgeon touches the wand tip to the reference divot, and then to each fiducial marker divot. This permits the image-guided workstation to correlate the actual physical location of the patient's skull to the preoperative images. The physician can then use the wand, in conjunction with the image-guided workstation, to locate an appropriate entry point and trajectory to the target in the brain.

One problem with the above registration procedure is the discomfort caused to the patient by the presence of the fiducial marker shaft extending upward from the bone-screw portion of the fiducial marker for receiving the screw-on imaging sphere and the screw-on divot. The upwardly-extending fiducial marker shaft can cause irritation to the patient's scalp. The presence of external threads on the shaft may increase the level of this irritation. Moreover, because there may be a long time period between preoperative imaging and the subsequent surgical procedure, the patient's scalp may be sewn up during the interim. Thus, the patient may experience such discomfort for an extended period of time. For these and other reasons, which will become apparent upon reading the following detailed description and viewing the drawings that form a part thereof, the present inventors have recognized an unmet need for fiducial marker devices, tools, and methods that reduce or avoid patient discomfort.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

FIG. 1 is a cross-sectional schematic diagram illustrating generally, by way of example, but not by way of limitation, one embodiment of an anchoring base portion of a fiducial marker assembly, and portions of an environment in which it is used.

FIG. 2 is a schematic diagram illustrating generally, by way of example, but not by way of limitation, one embodiment of a top view of the base illustrated in FIG. 1.

FIG. 3 is a cross-sectional schematic diagram illustrating generally, by way of example, but not by way of limitation, one embodiment in which a fiducial marker assembly includes a imagable or otherwise locatable spherical or other fiducial marker at a proximal end of a downwardly extending shaft.

FIG. 4 is a cross-sectional schematic diagram illustrating generally, by way of example, but not by way of limitation, one embodiment in which a fiducial marker assembly includes a registration receptacle at a proximal end of a downwardly extending shaft.

FIG. 6 is a cross-sectional and side view schematic diagram illustrating generally, by way of example, but not by way of limitation, one embodiment of an alternative base having a substantially cylindrical externally-threaded outer portion and a blunt bottom portion.

FIG. 7 is a side view schematic diagram illustrating generally, by way of example, but not by way of limitation, one embodiment of a guide tube for assisting in disposing a base.

FIG. 12A is a cross-sectional view schematic diagram illustrating generally, by way of example, but not by way of limitation, one embodiment of a screw-in base including a flange located above the top surface of a skull and an externally-threaded shaft extending outwardly above the top surface of the skull for receiving a screw-on fiducial marker, a registration receptacle, or the like.

FIG. 12B is a cross-sectional view schematic diagram further illustrating generally, by way of example, but not by way of limitation, one embodiment of an atraumatic cap overlying a raised portion of a shaft.

FIG. 13 is a schematic diagram illustrating generally an alternative embodiment of a base in which the mounting receptacle includes an alternative engagement mechanism; FIG. 13 also illustrates a compatible registration receptacle assembly, fiducial marker assembly, and base insertion tool portion

DETAILED DESCRIPTION

Figure 5:
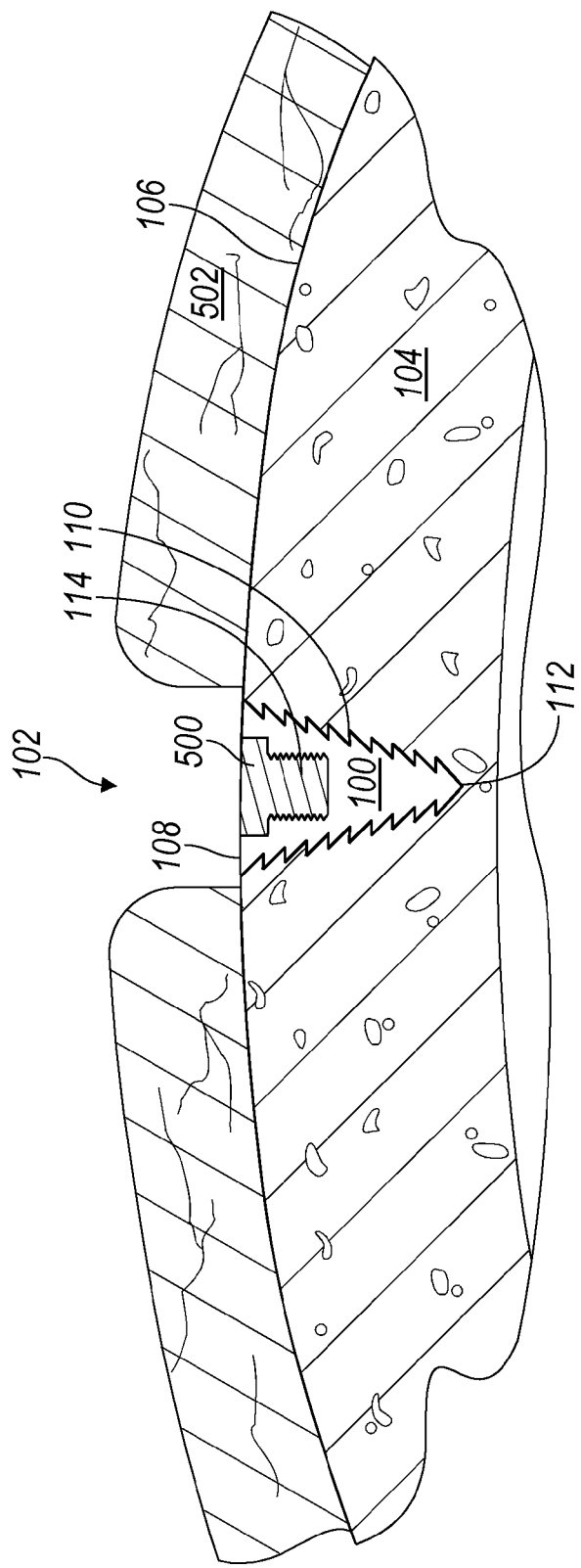
FIG. 5 is a cross-sectional schematic diagram illustrating generally, by way of example, but not by way of limitation, one embodiment in which a fiducial marker assembly includes a plug sized and shaped and sufficiently compliant to be press-fit into a mounting receptacle to prevent the accumulation of biological material or other debris therein when neither the fiducial marker nor the registration receptacle is screwed into the mounting receptacle.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the scope of the present invention. The following detailed description is, therefore, not to be taken in a limiting sense, and the scope of the present invention is defined by the appended claims and their equivalents.

In this document, the terms "a" or "an" are used, as is common in patent documents, to include one or more than one. Furthermore, all publications, patents, and patent documents referred to in this document are incorporated by reference herein in their entirety, as though individually incorporated by reference. In the event of inconsistent usages between this documents and those documents so incorporated by reference, the usage in the incorporated reference(s) should be considered supplementary to that of this document; for irreconcilable inconsistencies, the usage in this document controls FIG. 1 is a cross-sectional schematic diagram illustrating generally, by way of example, but not by way of limitation, one embodiment of an anchoring base 100 portion of a fiducial marker assembly 102, and portions of an environment in which fiducial marker assembly 102 is used. In the example of FIG. 1, base 100 is sized and shaped for being implanted in a patient's skull 104, either flush with, or recessed from, an outer surface 106 of skull 104. For example, as illustrated in FIG. 1, base 100 does not include any lip or shaft extending upward from outer surface 106 of skull 104. Instead, top portion 108 of base 100 is sized and shaped and threaded such that it can be implanted either flush with, or recessed from, an outer surface 106 of skull 104. In this example, base 100 includes a self-tapping or other externally threaded outer portion 110 extending distally outward from top portion 108 of base 100. In one embodiment, outer portion 110 of base 100 is conically-tapered toward a relatively sharp distal tip 112, as illustrated in FIG. 1, thereby allowing self-drilling, such as by using a manual or power-driven insertion tool. In another embodiment, outer portion 110 of base 100 is substantially cylindrical, such that it terminates at a relatively flat distal tip 112. In such an embodiment, base 100 may, but need not, include self-tapping external threads. In the example illustrated in FIG. 1, base 100 also includes an internally threaded receptacle 114 extending distally into base 100 from top portion 108 of base 100.

FIG. 2 is a schematic diagram illustrating generally, by way of example, but not by way of limitation, one embodiment of a top view of the base 100 illustrated in FIG. 1. FIG. 2 illustrates receptacle 114 in top surface 108 of base 100, together with at least one tool-receiving receptacle (such as a slot, hex receptacle, keyhole, or the like) for unscrewing base 100 from skull 104 (or, alternatively, for screwing base 100 into skull 104). In this example, the illustrated tool-receiving receptacle includes four slots 200A-D, such as for receiving portions of a Phillips-type screwdriver tip therein for unscrewing base 100 from skull 104. However, other examples could include two slots 200 or a different number of slots 200.

FIG. 3 is a cross-sectional schematic diagram illustrating generally, by way of example, but not by way of limitation, one embodiment in which fiducial marker assembly 102 includes a imagable or otherwise locatable spherical or other fiducial marker 300 at a proximal end of a downwardly extending shaft 302. Shaft 302 includes an externally threaded distal portion that is sized and shaped to be screwed into receptacle 114 of base 100. In one example, shaft 302 also includes a flange or other stop 304 that limits the travel of the distal end of shaft 302 into receptacle 114, thereby defining the height of the center of spherical fiducial marker 300 from stop 304. In another example, stop 304 is omitted, such that completely screwing shaft 302 into receptacle 114 defines a height of the center of spherical fiducial marker from the bottom of receptacle 114. Illustrative examples of marker 300 include: a magnetic resonance imaging (MRI) visible marker, such as for use in obtaining preoperative or other MRI images; a computed tomography (CT) visible marker, such as for use in obtaining preoperative or other CT images; an X-ray visible marker, such as for use in obtaining preoperative or other radiographic images; a light or other electromagnetic radiation emitting (or reflective) marker for serving as a remotely detectable locatable fiducial marker (e.g., using an optical positioning system during patient registration or subsequent surgical intervention in the operating room); a sensor, such as a coil or other magnetic field sensor, for sensing an externally provide test stimulus for providing position information (e.g., using a magnetic field generator and accompanying magnetic field-based positioning system during patient registration or subsequent surgical intervention in the operating room).

FIG. 4 is a cross-sectional schematic diagram illustrating generally, by way of example, but not by way of limitation, one embodiment in which fiducial marker assembly 102 includes a registration receptacle 400 at a proximal end of a downwardly extending shaft 402. Shaft 402 includes an externally threaded distal portion that is sized and shaped to be screwed into receptacle 114 of base 100. In one example, shaft 402 also includes a flange or other stop 404 that limits the travel of the distal end of shaft 402 into receptacle 114, thereby defining the height of the center (e.g., point of maximum depression) of registration receptacle 400 from stop 304 to be the same as the height of the center of fiducial marker 300 from stop 304. In another example, stop 404 is omitted, such that completely screwing shaft 402 into receptacle 114 defines a height of the center of the registration receptacle 400 from the bottom of mounting receptacle 114. In one example, registration receptacle 400 is sized and shaped to receive a sharp tip portion of a wand used in the operating room in conjunction with the image-guided workstation.

FIG. 5 is a cross-sectional schematic diagram illustrating generally, by way of example, but not by way of limitation, one embodiment in which fiducial marker assembly 102 includes a plug 500, sized and shaped and sufficiently compliant to be press-fit into mounting receptacle 114 to prevent the accumulation of biological material or other debris therein when neither fiducial marker 300 or registration receptacle 400 is screwed into receptacle 114. In this example, plug 500 is sized and shaped to be flush with top portion 108 of base 100. In one embodiment, plug 500 includes at least one soft portion that is sufficiently compliant to allow a needle or other tool to pierce or otherwise be inserted into and/or along plug 500 to pull plug 500 out of mounting receptacle 114. In one example, plug 500 also includes portions that are sized and shaped to fill slots 200A-D, as well as an interior portion of mounting receptacle 114. In one operative example, a physician press-fits plug 500 into place before suturing scalp 502 closed. This may be desirable, for example, between preoperative imaging and the subsequent surgical procedure, which may be separated by an arbitrarily long period of time.

FIG. 6 is a cross-sectional and side view schematic diagram illustrating generally, by way of example, but not by way of limitation, one embodiment of an alternative base 600 having a substantially cylindrical externally-threaded outer portion 602 and blunt bottom portion 604, as discussed above. In this example, base 600 also includes mounting receptacle 114 and top portion 108. FIG. 6 also illustrates a base insertion tool 606, which includes a proximal handle 608, a shaft 610, and an externally-threaded distal tip 612 sized and shaped to be threadedly received into mounting receptacle 114. In one example handle 608 is detachable from shaft 610. In one example, base insertion tool 606 is threaded (e.g., clockwise) into mounting receptacle 114. Base insertion tool 606 is then used to thread base 600 (e.g., clockwise) into a portion drilled in skull 104 such that top portion 108 of base 600 is flush to or recessed from a top surface 106 of skull 104. Base insertion tool 606 is then unthreaded (e.g., counter-clockwise) from mounting receptacle 114.

FIG. 7 is a side view schematic diagram illustrating generally, by way of example, but not by way of limitation, one embodiment of a guide tube 700 for assisting in disposing base 100 and/or base 600. Guide tube 700 includes a lumen 702 extending longitudinally therethrough. Lumen 702 is sized and shaped to allow base 100 and/or base 600 to pass therethrough. In this example, guide tube 700 includes a beveled distal tip 704, which is sized and shaped to align lumen 702 of guide tube 700 to a portal in the patient's scalp. In this illustrative example, guide tube 700 also includes a flange 706 extending radially outward circumferentially around a portion of guide tube 700 near beveled distal tip 704. In one example, flange 706 is fixedly positioned at a distance from beveled distal tip 704; this distance is selected such that flange 706 stabilizes a portion of the patient's scalp near the portal therein when beveled distal tip 704 of guide tube 700 is pressed into a portion of the portal in the patient's scalp. In another example, flange 706 is slidable longitudinally along guide tube 700 (e.g., like a washer, or the like, circumferentially surrounding guide tube 700) such that, by pushing downward on slidable flange 706, the physician can stabilize the portion of the patient's scalp near the portal therein when beveled distal tip 704 of guide tube 700 is pressed into a portion of the portal in the patient's scalp.

Figure 8:
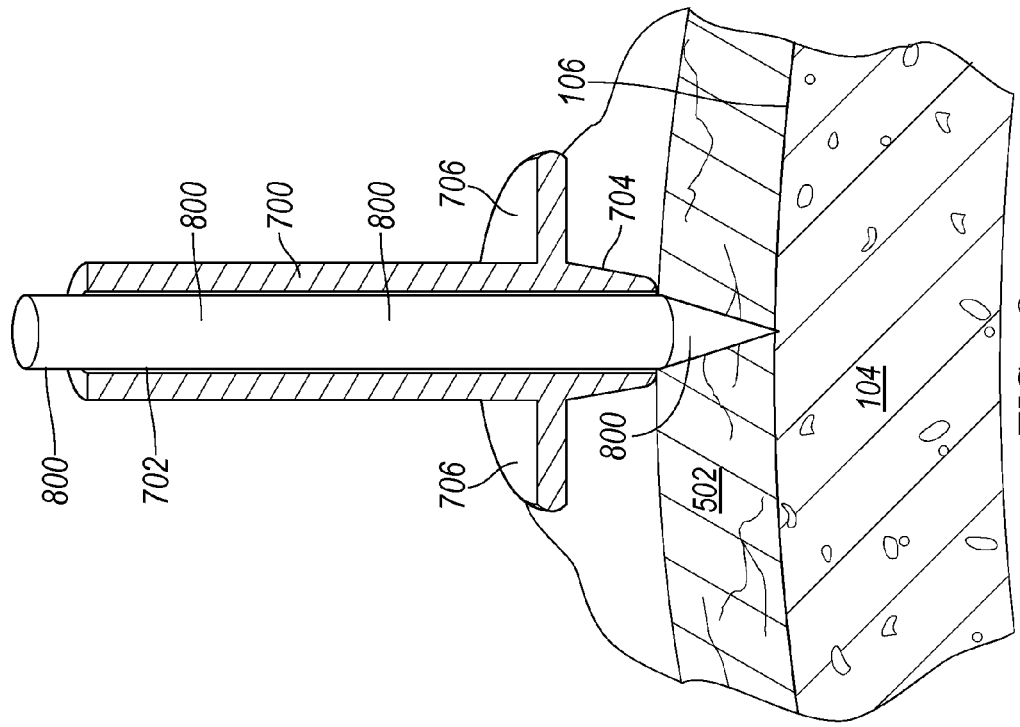
FIG. 8 is a side view schematic diagram illustrating generally, by way of example, but not by way of limitation, insertion of a sharp instrument such as a trocar or the like through a lumen of a guide tube for piercing a portal in a scalp.

FIG. 8 is a side view schematic diagram illustrating generally, by way of example, but not by way of limitation, insertion of a sharp instrument such as a trocar 800 or the like through lumen 702 of guide tube 700 for piercing a portal in scalp 502.

Figure 9:
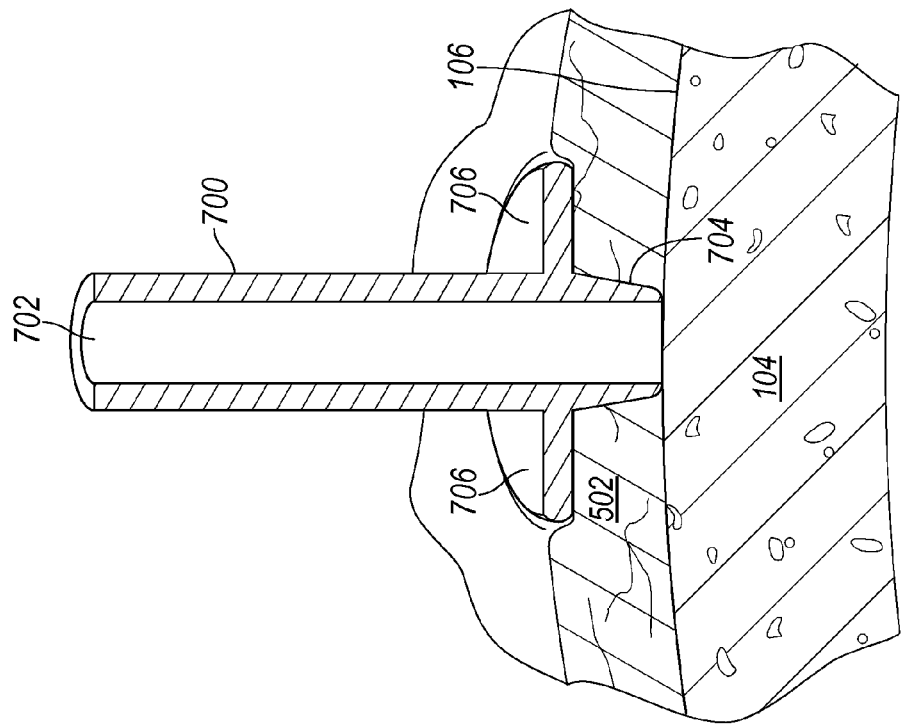
FIG. 9 is a side view schematic diagram illustrating generally, by way of example, but not by way of limitation, one embodiment in which a beveled distal tip of a guide tube is inserted into a scalp portal.

FIG. 9 is a side view schematic diagram illustrating generally, by way of example, but not by way of limitation, one embodiment in which beveled distal tip 704 of guide tube 700 inserted into the portal in scalp 502 that was created by trocar 800. Flange 706 stabilizes a portion of scalp 502 around the portal, either by virtue of its distance from the beveled distal tip 704, or by virtue of flange 706 being slidably pushed downward by the physician.

Figure 10:
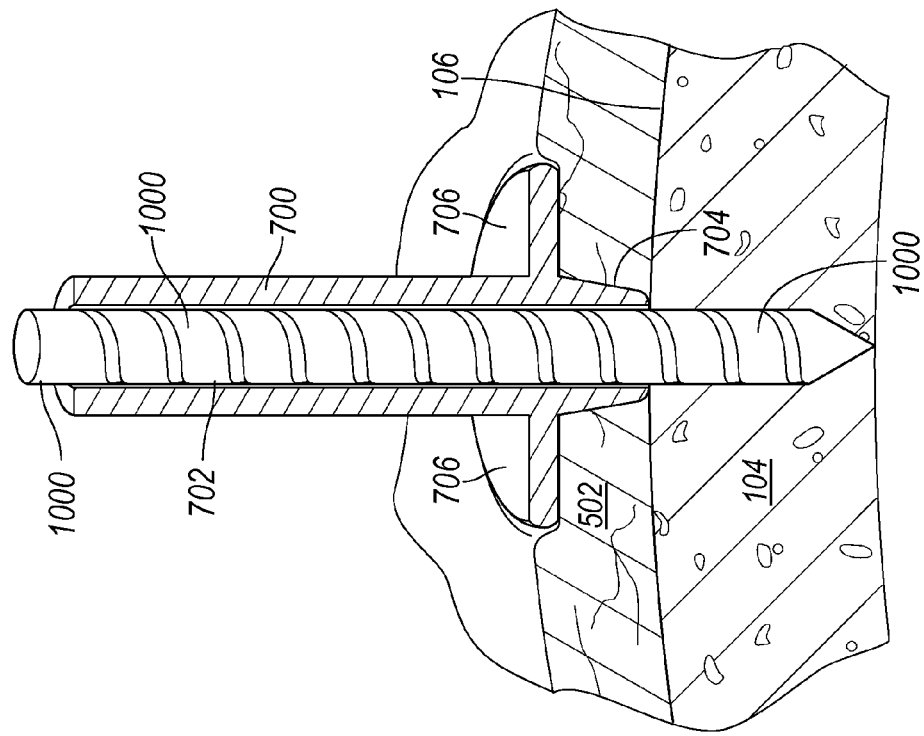
FIG. 10 is a side view schematic diagram illustrating generally, by way of example, but not by way of limitation, one embodiment in which a drill bit is inserted through a lumen of a guide tube for drilling into a skull while a scalp is being stabilized by a slidable or a fixed flange.

FIG. 10 is a side view schematic diagram illustrating generally, by way of example, but not by way of limitation, one embodiment in which drill bit 1000 is inserted through lumen 702 of guide tube 700 for drilling into skull 104 while a portion of scalp 502 is being stabilized by slidable or fixed flange 706.

Figure 11:
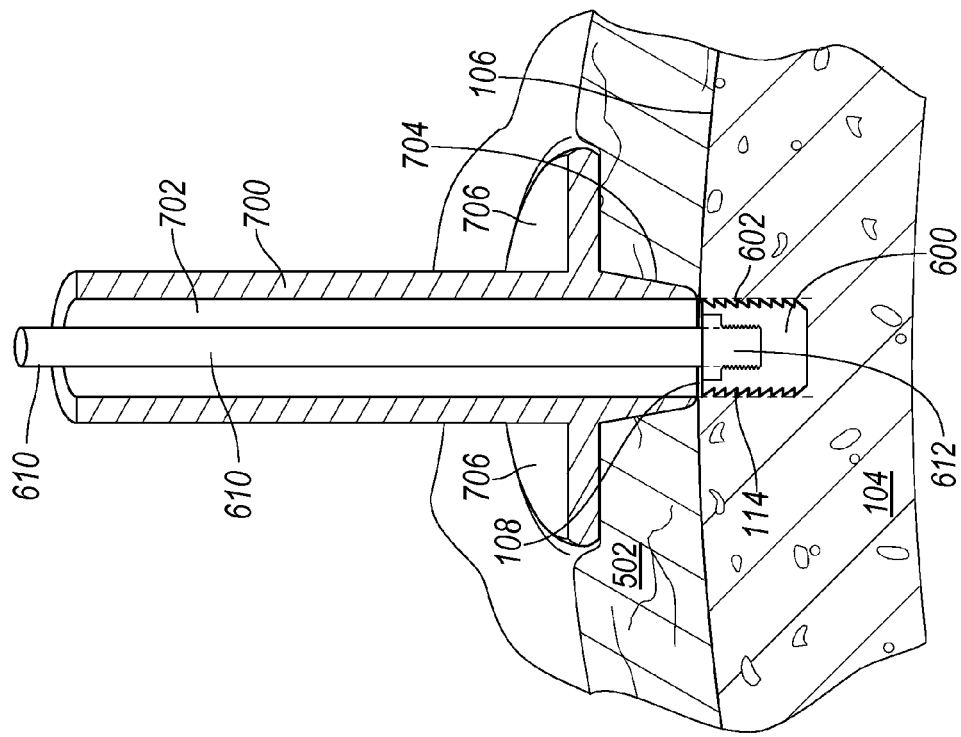
FIG. 11 is a side view schematic diagram illustrating generally, by way of example, but not by way of limitation, one embodiment in which a base is inserted into the drilled-out portion of a skull such that a top portion of the base is flush with or recessed from an outer surface of the skull.

FIG. 11 is a side view schematic diagram illustrating generally, by way of example, but not by way of limitation, one embodiment in which base 600 is inserted into the drilled-out portion of skull 104 such that top portion 108 is flush with or recessed from outer surface 106 of skull 104. In this example, base 600 is first screwed onto distal tip 612 of base insertion instrument shaft 610, then inserted through lumen 702 of guide tube 700. Base 600 is then threaded into the drilled-out portion of skull 104 by screwing it in using base insertion instrument 606, while scalp 502 is being stabilized by flange 706. Distal tip 612 of shaft 610 of base insertion instrument 606 is then unscrewed from base 600, and shaft 610 is withdrawn from lumen 702 of guide tube 700.

Although FIGS. 10 and 11 illustrate drilling out a portion of skull 104 to insert a base 600, alternatively, a self-drilling base (e.g., base 100) is used, so that no separate drilling step is required. Self-drilling base 100 is placed on the distal tip 612 of base insertion instrument 606, which may include a power-driven screwdriver to rotate shaft 610 of base insertion instrument 606, so as to screw base 100 into skull 104, such that top portion 108 of base 100 is flush with or recessed from outer surface 106 of skull 104. This flush or recessed mounting improves patient comfort, particularly if scalp 502 is to be sewn up, such as where there is an extended period of time between preoperative imaging and the subsequent surgical procedure.

FIGS. 12A and 12B illustrate an alternative solution to providing patient comfort. FIG. 12A is a cross-sectional view schematic diagram illustrating generally, by way of example, but not by way of limitation, one embodiment of a screw-in base 1200 including a flange 1202 located above the top surface 106 of skull 104 and an externally-threaded shaft 1204 extending outwardly above top surface 106 of skull 104 for receiving a screw-on fiducial marker, a registration receptacle, or the like. FIG. 12B is a cross-sectional view schematic diagram further illustrating generally, by way of example, but not by way of limitation, one embodiment of an atraumatic cap 1206 overlying the raised portion of shaft 1204. In one example, cap 1206 is made of a material that is compliant enough to allow it to be press-fit onto and over shaft 1204 and flange 1202. In this example, the underside of cap 1206 is sized and shaped to be conformal to shaft 1204, flange 1202, and any other features of the fiducial marker base being covered. The top of cap 1206 is hemispherically or otherwise tapered at an acute enough angle with top surface 106 of skull 104 such that discomfort to nearby portions of the patient's scalp 502 is reduced or avoided altogether.

FIG. 13 is a schematic diagram illustrating generally, by way of example, but not by way of limitation, an alternative embodiment of base 1300 in which mounting receptacle 1302 is not internally threaded, but instead includes an alternative engagement mechanism. In this example, the alternative engagement mechanism includes female snap-fit receptacles 1304A-B formed into the sidewalls of the interior of mounting receptacle 1302. FIG. 13 also illustrates a registration receptacle assembly 1306, including a divot-like registration receptacle 1308, a shaft 1310, and male snap-fit protrusions 1312A-B configured to be snap-fit into corresponding female snap-fit receptacles 1304A-B of mounting receptacle 1302. (Of course, male and female snap-fit connections can be interchanged such that mounting receptacle 1302 includes male snap-fit protrusions configured for receiving female snap-fit receptacles thereupon.) A portion of shaft 1310 is split, providing sufficient compliance to permit the snap-fit operation. FIG. 13 also illustrates a fiducial marker assembly 1314 including a locatable fiducial marker 1316, a split shaft 1318, and male protrusions or other snap-fit features 1318A-B for engaging corresponding mating features (e.g., 1304A-B) in mounting receptacle 1302. FIG. 13 also illustrates a portion of a base insertion tool 1320 (analogous to 606), including a shaft 1322 having a split-shaft portion 1324, and male protrusions or other snap-fit features 1318A-B for engaging corresponding mating features (e.g., 1304A-B) in mounting receptacle 1302. Mounting receptacle 1302 need not be limited to threaded and snap-fit engagement devices, but could include any other known engagement devices or structures.

In a further example, a trajectory guide can be mounted to one or more of the bases described herein, such as by using a suitably sized and shaped screw or press-fit bolt that couples a base portion of the trajectory guide to the mounting receptacle. One embodiment of a suitable ball-and-socket trajectory guide is described in Truwit U.S. Pat. No. 6,267,769, the disclosure of which is incorporated by reference herein in its entirety, including its discussion of a ball-and-socket trajectory guide. Another example of a suitable trajectory guide is described in Skakoon et al. U.S. patent application Ser. No. 09/828,451, filed on Apr. 6, 2001 and assigned to Image-Guided Neurologics, Inc., the disclosure of which is incorporated herein by reference in its entirety, including its disclosure of a rotatable saddle trajectory guide.

Figure 14:
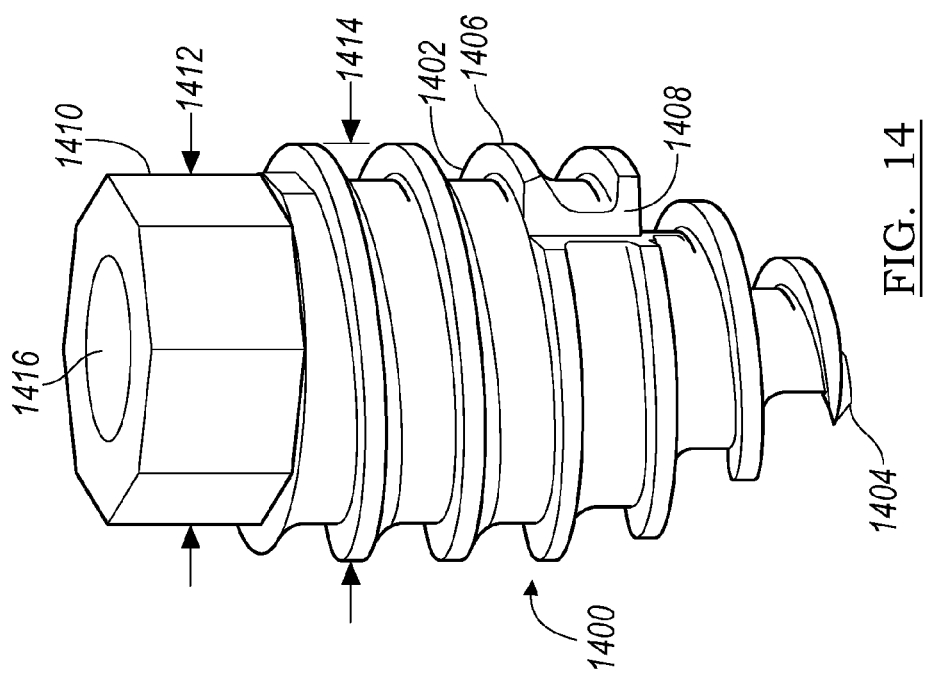
FIG. 14 is a schematic drawing illustrating generally another example of an anchoring base portion of a fiducial marker assembly.

FIG. 14 is a schematic drawing illustrating generally, by way of example, but not by way of limitation, another example of an anchoring base 1400 portion of a fiducial marker assembly 102. In this example, the stainless steel or other base 1400 includes a distal portion 1402 that tapers toward a sharp tip 1404. The distal portion 1402 includes self-tapping and/or self-drilling external spiral threads 1406. In this example, the threads 1406 include one or more channels across one or more of the threads 1406. This permits transport of bone or other material across the one or more threads 1406 when the anchoring base 1400 is inserted into the skull or into some other surface.

In this example, the base 1400 also includes a proximal head portion 1410. The head 1410 includes a faceted outer periphery or circumference (e.g., hexagonal, octagonal, etc.) that is sized and shaped to be received within and engaged by a correspondingly-sized socket-like driver or like device. The driver socket rotates the base 1400, which, in turn, threads the base 1400 into the skull. If desired, a starter hole can first be drilled into the skull for receiving the base 1400, however, this is not required. In this example, the outer periphery or circumference 1412 of the head 1410 is smaller than the outer circumference 1414 of the threads 1406. This permits the base 1400 to be introduced such that the proximal surface of the head 1410 is flush with or recessed from the outer surface of the subject's skull, if desired, such as discussed above. In an alternate example, the head 1410 could include a non-circular outer surface that is sized and shaped to be received within and engaged by a correspondingly-sized socket-like driver or like device.

In one example, the outer circumference 1412 of the head 1410 is sufficiently small to allow a thin-walled socket to be slipped over the head 1410 for screwing the base 1400 into the skull (or unscrewing it therefrom). In one such example, the outer circumference of such a socket is small enough to permit sinking of the head 1410 such that the proximal surface of the head 1410 is flush with or recessed from the outer surface of the subject's skull, if desired, as discussed above. Although FIG. 14 illustrates a flush or recessed fiducial marker base using a head that can be engaged by a socket, in an alternate example, such a head need not permit the base 1400 to be flush or recess mounted.

In FIG. 14, the head 1410 includes a receptacle 1416 for receiving an apparatus including an imagable and/or remotely detectable locator, a registration divot, or the like. For receiving such an apparatus, a portion of the receptacle 1416 includes internal threads, a snap-fitting, or any other engagement device, such as discussed above.

Figure 15:
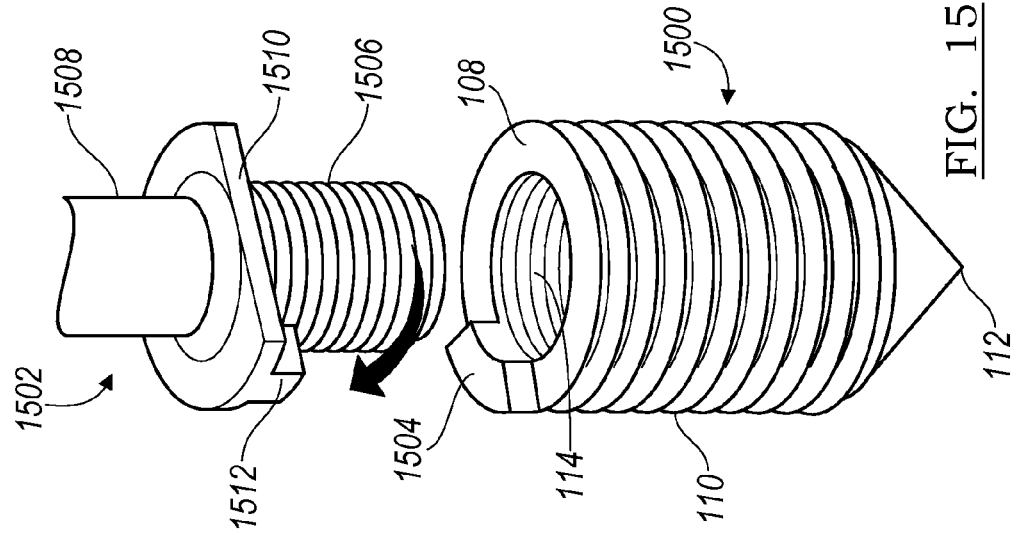
FIG. 15 is a schematic diagram illustrating generally another anchoring base, together with a distal portion of an accompanying driver for inserting the anchoring base.

FIG. 15 is a schematic diagram illustrating generally, by way of example, but not by way of limitation, another anchoring base 1500, together with a distal portion of an accompanying driver 1502 for inserting the anchoring base 1500 into the skull, a bone, or other material. The anchoring base 1500 is similar, in certain respects, to the anchoring base 100 of FIGS. 1 and 2. However, in the example illustrated in FIG. 15, the anchoring base 1500 includes a rectangular or other step 1504 extending upward from the top surface 108 of the base 1500. In the illustrated example, the step 1504 extends radially outward from the receptacle 114 to the outer portion 110 of the base 1500.

In the example of FIG. 15, the stainless steel or other driver 1502 includes an externally threaded distal end 1506 extending outward from a shaft 1508. The threaded distal end 1506 is sized and shaped for being inserted and threaded into the internally threaded receptacle 114 of the base 1500. In this example, the driver 1502 includes a flange 1510 between the shaft 1508 and the threaded distal end 1506. The flange 1510 includes a radially protruding step 1512. This radial step 1512 is sized and shaped for engaging the step 1504 on the top surface 108 of the base 1500 when the threaded distal end 1506 of the driver 1502 is fully inserted into the internally threaded receptacle 114 of the base 1500. Such engagement assists in transferring force from the driver 1502 to the base 1500 as both are being rotated for screwing the base 1500 into the skull, bone, or other desired material.

Figure 16:
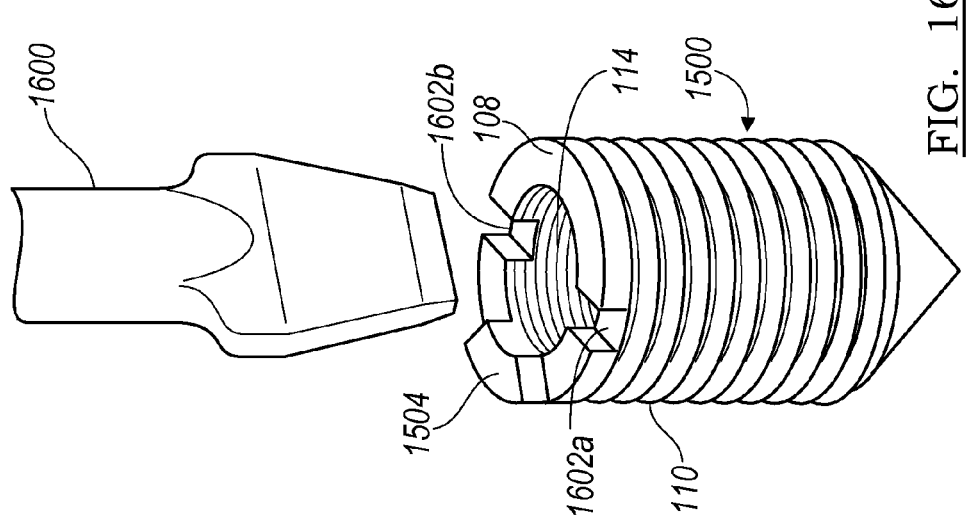
FIG. 16 is a schematic diagram illustrating generally a further example of the anchoring base and a stainless steel or other flat-tipped screwdriver, or other base extraction device.

FIG. 16 is a schematic diagram illustrating generally, by way of example, but not by way of limitation, a further example of the anchoring base 1500 and a stainless steel or other flat-tipped screwdriver, or other base extraction device 1600. In this example, the top surface 108 of the base 1500 additionally includes extraction slots 1602A-B. In the illustration of FIG. 16, each of the slots 1602A-B extends radially outward from the receptacle 114 to respective locations on the outer portion 110 of the base 1500. The slots 1602A-B are located on opposite sides of the base 1500 and are aligned with each other. This permits the extraction device 1600 to be concurrently inserted into both of the slots 1602A-B, such as for unscrewing the base 1500 from the skull, bone, or other desired material in which it was previously inserted.

Figure 17:
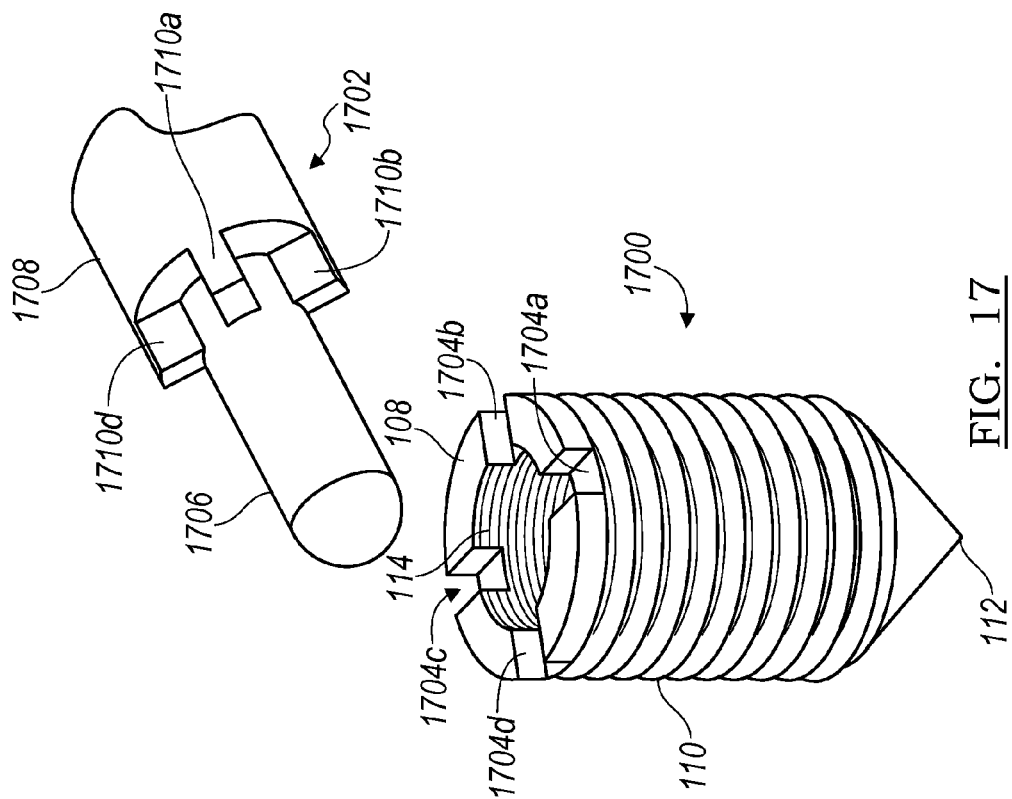
FIG. 17 is a schematic diagram illustrating generally another anchoring base, together with a distal portion of an accompanying driver/extractor tool for inserting the anchoring base into the skull, a bone, or other material, and/or for extracting the anchoring base therefrom.

FIG. 17 is a schematic diagram illustrating generally, by way of example, but not by way of limitation, another anchoring base 1700, together with a distal portion of an accompanying driver/extractor tool 1702 for inserting the anchoring base 1700 into the skull, a bone, or other material, and for extracting the anchoring base 1700 therefrom. The anchoring base 1700 is similar, in certain respects, to the anchoring base 100 of FIGS. 1 and 2. However, in the example illustrated in FIG. 17, the top surface 108 of the base 1700 includes slots 1704A-D. In the illustration of FIG. 17, each of the slots 1704A-D extends radially outward from the receptacle 114 to respective locations on the outer portion 110 of the base 1700. In this example, the slots 1704A and 1704C are located on opposite sides of the base 1700 and are aligned with each other. Similarly, the slots 1704B and 1704D are located on opposite sides of the base 1700 and are aligned with each other. Therefore, in this example, a line conceptually defined to extend through the slots 1704A and 1704C would orthogonally intersect a line conceptually defined to extend through the slots 1704B and 1704D, thereby dividing the top surface 108 of the base 1700 into quadrants.

In this example, the stainless steel or other tool 1700 includes a rounded cylindrical distal tip 1706 extending longitudinally outward from a slightly larger diameter shaft 1708. In this example, the tip 1706 is sized and shaped to fit within the receptacle 114 of the base 1700, but does not include external threads for engaging the internal threads within the receptacle 114. The tool 1700 includes steps or teeth 1710A-D extending downward from the shaft 1708 such that the teeth 1710A-D engage respective slots 1704A-D of the base 1700 when the distal tip 1706 is inserted within the receptacle 114 of the base 1700. This allows the driver 1702 to transmit force to the base 1700 upon rotation of the driver 1702 by the user for screwing the base 1700 into the skull, bone, or other material, or (by reversing the direction of the rotation), for unscrewing the base 1700 therefrom.

In one example, the rounded cylindrical distal tip 1706 is constructed of a deformable material such as soft plastic or vulcanized rubber. In this embodiment, the distal tip 1706 is sized and shaped to snugly fit within the receptacle 114 of the base 1700. When the distal tip 1706 is inserted within the receptacle 114, it is rotated by the tool 1702. The compliant distal tip 1706 snugly engages the internal threads of receptacle 114. The deformable material of the distal tip 1706 grasps the internal threads to hold assembly 102 affixed to the driver 1702 during insertion of the assembly 102 into the skull, bone, or other receiving material. Once assembly 102 is inserted, counter-rotation of the distal tip 1706 of driver 1702 disengages the distal tip 1706 from the snug fitting with the internal threads of receptacle 114. In alternate examples, a distal tip constructed of a deformable material could be used to grasp the surfaces of a complementary receptacle to affix the assembly to a driver; such surfaces need not be threaded.

Figure 19:
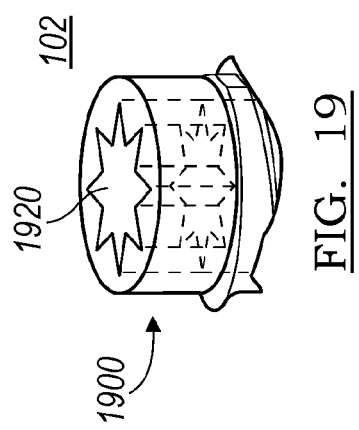
FIG. 19 is a schematic diagram illustrating generally another example of an anchoring base having a ten pointed 'star' type orifice for engagement with a driver/extractor tool.
Figure 20:
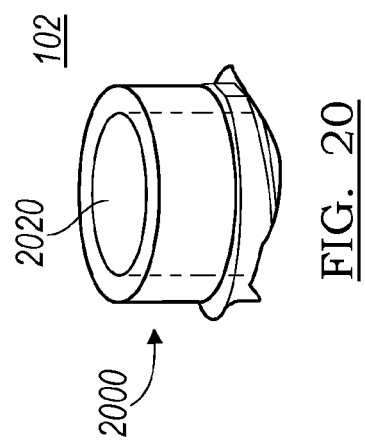
FIG. 20 is a schematic diagram illustrating generally another example of an anchoring base having an oval-shaped orifice for engagement with a driver/extractor tool.
Figure 18:
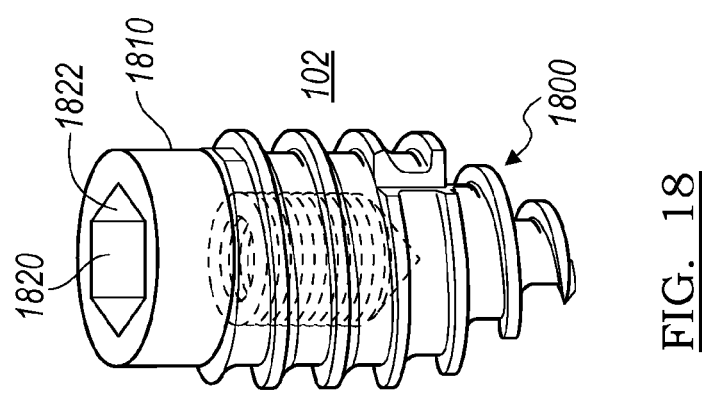
FIG. 18 is a schematic diagram illustrating generally another example of an anchoring base having a hexagonal orifice for engagement with a driver/extractor tool.

FIG. 18 is a schematic drawing illustrating generally, by way of example, but not by way of limitation, another example of an anchoring base 1800 portion of a fiducial marker assembly 102. The example depicted in FIG. 18 includes a proximal head 1810 with a non-circular orifice 1820. The head 1810 includes an internal surface 1822 (e.g. hexagonal, oval-shaped, etc.) defining the internal periphery of the orifice 1820. The surface 1822 is sized and shaped to receive and engage a correspondingly-sized driver or like device. FIG. 18 presents an assembly 102 having a hexagonal orifice 1820. FIG. 19 presents an assembly 102 having a 10 pointed 'star' or other toothed orifice 1920 or the like. The internal peripheral surface of the orifice 1820 need not be vertical. In a further example, the orifice 1820 tapers inward in the direction of the distal tip, similar to a drill chuck-key receptacle. FIG. 20 presents an assembly 102 having an oval-shaped orifice 2020 or the like. Because the examples of FIGS. 18-20 each present a non-circular orifice 1820, 1920, 2020, the bases 1800, 1900, 2000 and correspondingly-sized drivers will not rotate with respect to one another when engaged. Thus, the internal peripheries of the orifices in the bases 1800, 1900, 2000 are capable of engaging and rotating with correspondingly-sized drivers. Such engagement is believed to be less susceptible to slipping or stripping than, for example, a flat-head or Philips screwdriver type of engagement. Moreover, engagement of an internal orifice is believed to be more amenable to flush or recessed mounting than an external hex-head, for example, which would typically use a more difficult to manufacture thin-walled socket for affixing the base such that it is flush or recessed mounted.

Figure 21:
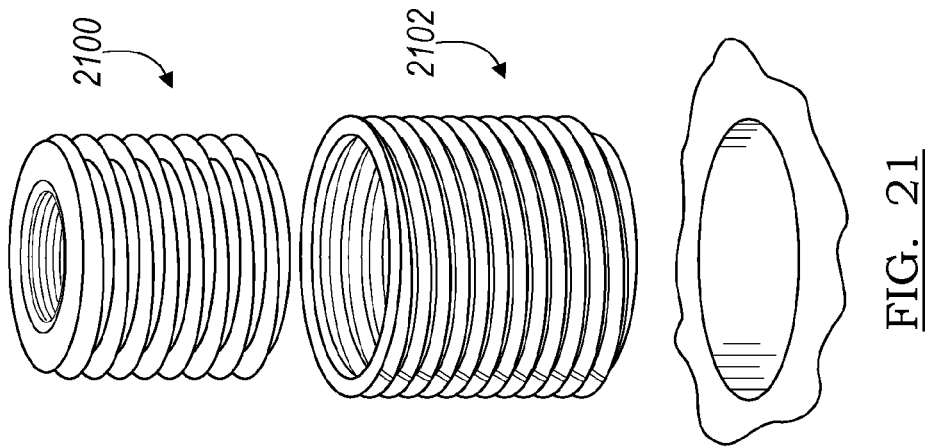
FIG. 21 is a schematic diagram illustrating generally another example of an anchoring base, together with a fastener for fixing the anchoring base to the skull.

FIG. 21 is a schematic diagram illustrating generally, by way of example, but not by way of limitation, another anchoring base 2100. In this example, an intermediate tubular fastener 2102, is sized and shaped for fixing the anchoring base 2100 to the skull or other desired bone. The inner circumferential surface of the fastener 2102 is sized and shaped to receive the threaded anchoring base 2100. The outer circumferential surface of the anchoring base 2100 has a perimeter slightly larger than the perimeter of the inner surface of fastener 2102. When the anchoring base 2100 is screwed into the fastener 2102, the anchoring base 2100 engages the inner surface of the fastener 2102. In one example, the fastener 2102 is constructed from a deformable helical coil of wire. In another example, the fastener 2102 is constructed from deformable plastic or rubber. The screwing engagement of the anchoring base 2100 to the fastener 2102 causes the fastener 2102 to deform and expand. The expansion of the fastener 2102 within the skull forces the fastener 2102 into a fixed engagement with the skull, which thereby fixes the anchoring base 2100 to the skull. In another option, the fastener 2102 is sized and shaped to receive an anchor for a trajectory guide or other apparatus, as described above.

Figure 23:
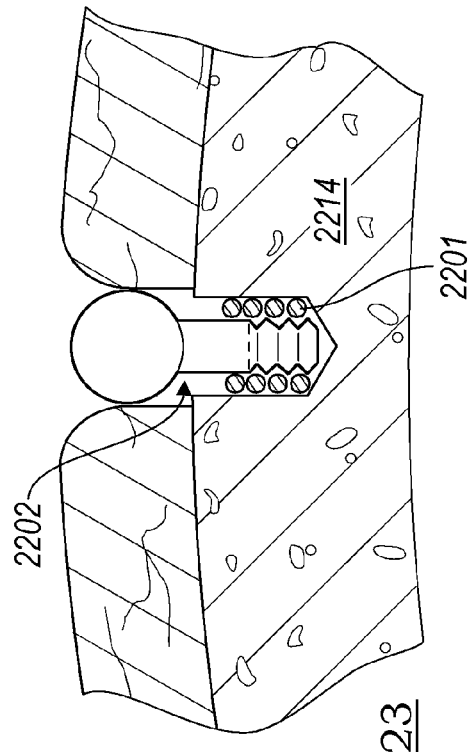
FIG. 23 is a schematic diagram illustrating generally the example of FIG. 22 inserted into a skull or other desired surface.
Figure 22:
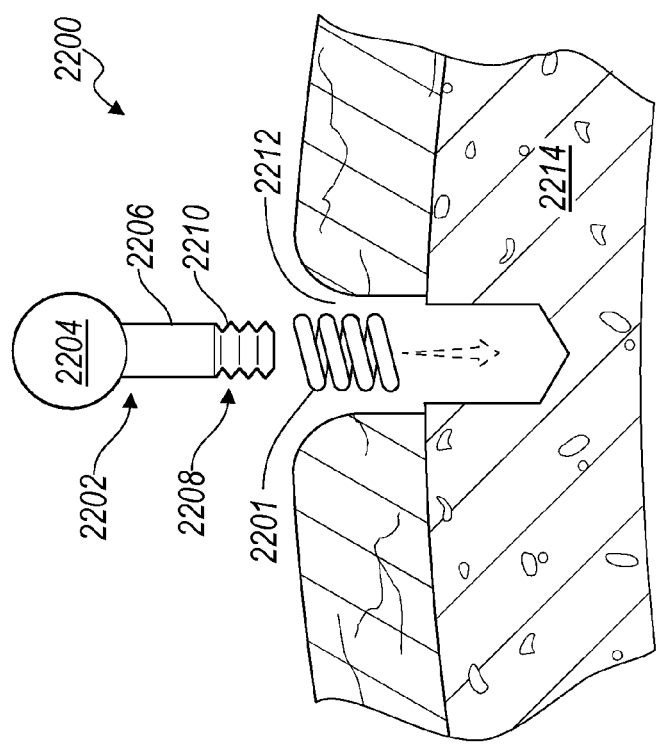
FIG. 22 is a schematic diagram illustrating generally another example of a fiducial marker assembly, including a helical coil or other expandable that acts as an anchoring base for an imagable fiducial marker.

FIG. 22 is a schematic diagram illustrating generally, by way of example, but not by way of limitation, another example including a fiducial marker assembly 2200. In this example, the fiducial marker assembly includes a helical coil 2201 (or other expandable fastener). The coil 2201 acts as an anchoring base for a fiducial marker 2202. The fiducial marker 2202 includes an imagable sphere 2204 and a shaft 2206 with a distal tip 2208 that includes external threads 2210. A hole 2212 is drilled into the skull or other desired surface 2214. The coil 2201 is inserted into the hole 2212, as illustrated in FIG. 23. The wire of the coil 2201 provides internal threads to receive the external threads 2210 of the distal tip 2208 of the shaft 2206 of the fiducial marker 2202. FIG. 23 illustrates the fiducial marker 2202 being screwed into the coil 2200. This expands the coil 2200 outward within the hole 2212 to create a firm affixation between the coil 2200 and the hole 2212.

Figure 25:
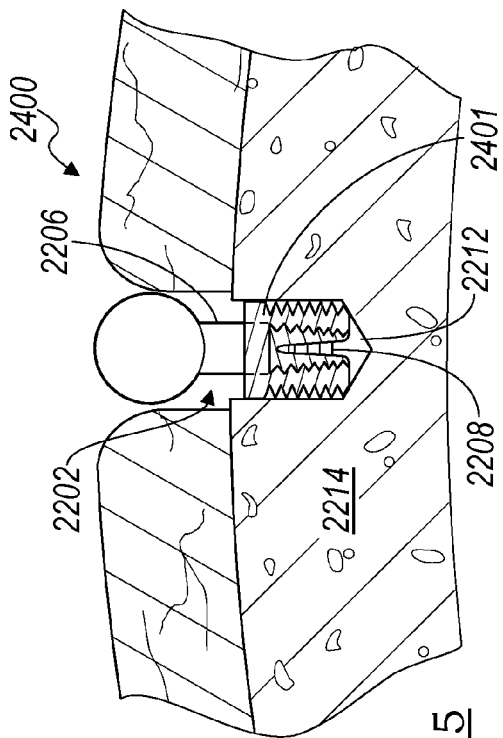
FIG. 25 is a schematic diagram illustrating generally the example of FIG. 24 inserted into a skull or other desired surface.
Figure 24:
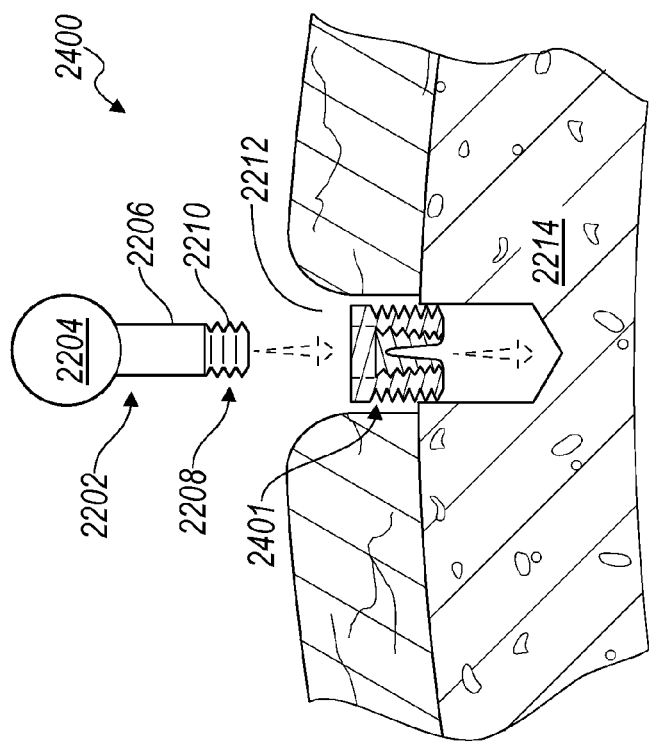
FIG. 24 is a schematic diagram illustrating generally another example of a fiducial marker assembly, including a jaw-like expandable fastener that acts as an anchoring base for an imagable fiducial marker.

FIG. 24 is a schematic diagram illustrating generally, by way of example, but not by way of limitation, another example including a fiducial marker assembly 2400. In this example, the fiducial marker assembly includes a jaw-like expandable fastener 2401. The fastener 2401 acts as an anchoring base for a fiducial marker 2202. A hole 2212 is drilled into the skull or other desired surface 2214. The fastener 2401 is inserted into the hole 2212, as illustrated in FIG. 24. The fastener 2401 includes internal threads to receive the external threads 2210 of the distal tip 2208 of the shaft 2206 of the fiducial marker 2202. These internal threads of the fastener 2401 taper inward slightly in a distal direction such that, when the distal tip 2208 of the shaft 2206 is inserted within the internal threads of the fastener 2401, the external threads of the fastener expand outward to engage the interior circumference of the hole 2212, as illustrated in FIG. 25.

It is to be understood that the above description is intended to be illustrative, and not restrictive. For example, the above-described embodiments may be used in combination with each other. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects.

What is claimed is:

1. A kit comprising:
   an anchoring base, sized and shaped to be implanted within a patient's skull such that a top surface of a top portion of the base is flush to or recessed from an outer surface of the patient's skull, the base including:
      an externally threaded outer portion;
      a distal tip;
      a tool engaging portion including the top surface of the base, the tool engaging portion having a rotatably engagable peripheral surface extending from the top surface of the base toward the distal tip;
      an engagable mounting receptacle in the top portion of the base;
   a plug sized and shaped to be received in the mounting receptacle and a plug removal tool, wherein the plug is formed of a compliant material to allow the plug to be press-fit into the mounting receptacle and be pierced by the removal tool to be removed with the plug removal tool; and
   an anchoring base insertion tool having an engaging portion to engage the tool engaging portion and the engagable mounting receptacle and a shaft coupled to and extending from the engaging portion;
   wherein the engaging portion of the anchoring base insertion tool has a deformable distal portion sized and shaped to fit in the engagable mounting receptacle and to be deformed by engagement with the engagable mounting receptacle so that the deformable portion snugly fits within the engagable mounting receptacle and operable to hold the anchoring base insertion tool to the anchoring base when the deformable distal portion is fitted against the engagable mounting receptacle;
   wherein engaging portion of the anchoring base insertion tool further has a drive portion operable to engage the tool engaging portion while the deformable distal portion is snugly retained in the engagable mounting receptacle of the anchoring base;
   wherein the tool engaging portion includes a proximal head, the head including the top portion of the base, the head presenting at least one rotatably engageable internal or external peripheral surface capable of being engaged to implant the base in a patient's skull.

2. The kit of claim 1, further including a fiducial marker, the fiducial marker including a fiducial marker shaft portion sized and shaped to be received and engaged into the mounting receptacle, the fiducial marker further including a flange extending from the fiducial marker shaft portion that engages the top portion of the anchoring base to limit travel of the shaft into the anchoring base.

3. The kit of claim 2, further including a registration receptacle having a registration receptacle shaft portion sized and shaped to be received and engaged into the mounting receptacle when the fiducial marker is removed from the mounting receptacle, the registration receptacle further including a flange extending from the registration receptacle shaft portion that engages the top portion of the anchoring base to limit travel of the registration receptacle shaft into the anchoring base.

4. The kit of claim 3, wherein the plug includes a main body portion having an exterior dimension to be substantially received within the engagable mounting receptacle when both of the fiducial marker and the registration receptacle are removed to provide a top surface that is substantially flush with the top surface of the mounting receptacle.

5. The kit of claim 1, in which the mounting receptacle is internally threaded.

6. The kit of claim 1, further including a trajectory guide coupled to the engagable mounting receptacle.

7. A kit comprising:
an anchoring base, sized and shaped to be implanted within a patient's skull such that a top surface of a top portion of the base is flush to or recessed from an outer surface of the patient's skull, the base including:
an externally threaded outer portion;
a distal tip;
a tool engaging portion including the top portion of the base, the tool engaging portion presenting at least one rotatably engagable internal surface or external peripheral surface capable of being engaged to implant the base in a patient's skull;
an engagable mounting receptacle in the top portion of the base; and
an anchoring base insertion tool having an engaging portion to engage the tool engaging portion and the engagable mounting receptacle and a shaft coupled to and extending from the engaging portion;
wherein the engaging portion of the anchoring base insertion tool has a deformable distal portion sized and shaped to fit in the engagable mounting receptacle and to be deformed by engagement with the engagable mounting receptacle so that the deformable portion snugly fits within the engagable mounting receptacle and operable to hold the anchoring base insertion tool to the anchoring base when the deformable distal portion is fitted against the engagable mounting receptacle;
wherein engaging portion of the anchoring base insertion tool further has a drive portion operable to engage the tool engaging portion while the deformable distal portion is snugly retained in the engagable mounting receptacle of the anchoring base.

8. The kit of claim 7, in which the rotatably engagable internal or external peripheral surface defines at least one non-circular orifice within the top portion of the base.

9. The kit of claim 8, in which the orifice is formed in the shape of at least one of hexagonal, star-shaped, toothed, polygonal, oval, or cruciform.

10. The kit of claim 7, wherein the patient's skull defines an outer surface relative to which the kit can be placed and in which the at least one rotatably engagable internal or external peripheral surface is positionable substantially vertical relative to the outer surface of the patient's skull when the base is affixed to the patient's skull.

11. The kit of claim 7, further including:
a fiducial marker, the fiducial marker including a shaft, at least a portion of the shaft sized and shaped to be received and engaged into the mounting receptacle; and
a registration receptacle including a shaft, at least a portion of the shaft sized and shaped to be received and engaged into the mounting receptacle;
wherein the fiducial marker and the registration receptacle are individually received and engaged in the mounting receptacle.

12. The kit of claim 7, further comprising a plug sized and shaped to be received in the mounting receptacle and a plug removal tool;
wherein the plug is constructed to allow the plug to be press-fit into the mounting receptacle;
wherein the plug is sufficiently compliant to allow the plug to be removed from the mounting receptacle by inserting the plug removal tool into the plug to assist in pulling the plug out of the mounting receptacle.

13. The kit of claim 7, further including a trajectory guide coupled to the engagable mounting receptacle.

14. The kit of claim 7, wherein the tool engaging portion includes a proximal head, the proximal head including the top surface of the base, the proximal head having a rotatably engagable peripheral surface extending from the top surface of the base toward the distal tip.

15. A kit comprising:
an anchoring base having an exterior surface extending from a top surface end to a second end and sized and shaped to be implanted within in a patient's skull such that a top surface is at least level with or below an outer surface of the patient's skull, the anchoring base including:
an externally threaded outer portion including a thread extending from the top surface end to the second end of the anchoring base;
a tool engaging portion;
a distal tip; and
an anchoring base receptacle extending from the top surface of the anchoring base defining a bore within the anchoring base;
a locatable fiducial marker, including a shaft extending from the fiducial marker, the shaft having a distal shaft portion sized and shaped to be received and engaged into the base receptacle, the shaft being sized and configured to separate the fiducial marker from the base by a first distance when the fiducial marker shaft is engaged into the anchoring base receptacle; and
a registration receptacle, separate from and interchangeable with the fiducial marker into the base receptacle, the registration receptacle includes a shaft extending from the registration receptacle, the shaft has a distal shaft portion sized and shaped to be received and engaged into the anchoring base receptacle when the fiducial marker shaft is not engaged into the base receptacle, the shaft being sized and configured to separate the registration receptacle from the base by the first distance when the registration receptacle shaft is engaged into the anchoring base receptacle;
a plug positioned in the anchoring base receptacle when the fiducial marker shaft and the registration receptacle shaft are not engaged to the anchoring base receptacle;
an anchoring base insertion tool having an engaging portion to engage the anchoring base receptacle and a shaft coupled to and extending from the engaging portion, wherein the anchoring base insertion tool has a deformable distal portion sized and shaped to snugly retain an engagement with the anchoring base receptacle when the deformable distal portion is fitted against the anchoring base receptacle and the base insertion tool further has a drive portion operable to engage a base drive portion of the anchoring base while the deformable distal portion is snugly retained in the anchoring base; and a guide tube, for assisting in disposing the anchoring base within the patient's skull, having:
an inner guide tube wall defining a lumen extending longitudinally through the guide tube and sized to allow passage of the anchoring base and guide the anchoring base to an anchoring location on the patient's skull;
an outer surface extending from a first terminal end to a second terminal end, wherein at least a portion of the outer surface defines a beveled distal tip operable to engage the patient's scalp to position the scalp a distance from an inner wall surface of the guide tube; and
a flange extending outwardly from the outer surface first terminal end that is selected such that the flange stabilizes a portion of the patient's scalp near a portal in the patient's scalp when the beveled distal tip of the guide tube is pressed into a portion of the portal in the patient's scalp and the first terminal end engages the patient's skull.

16. The kit of claim 15, further including a trajectory guide coupled to the anchoring base receptacle.

17. The kit of claim 15, further comprising:
a plug removal tool;
wherein the plug is sufficiently compliant to allow the plug to be removed from the base receptacle by inserting the plug removal tool into the plug and pulling on the tool to pull the plug out of the base receptacle.

18. The kit of claim 15, in which the flange is longitudinally slidable along the guide tube to select the distance from the beveled distal tip to stabilize a portion of the patient's scalp.

19. The kit of claim 18, further comprising a trajectory guide coupled to the anchoring base receptacle.

20. The kit of claim 15, wherein the anchoring base includes an outer threaded wall that tapers towards a central axis of the anchoring base from the top surface end to the second end.

21. The kit of claim 15, wherein the tool engaging portion includes a proximal head, the proximal head including the top surface of the base, the proximal head having a rotatably engagable peripheral surface extending from the top surface of the base toward the distal tip.

22. The kit of claim 15, wherein the tool engaging portion includes a proximal head, the proximal head including the top portion of the base, the proximal head presenting at least one rotatably engagable internal or external peripheral surface capable of being engaged to implant the base in a patient's skull.

23. A method of placing an anchoring base in a patient's skull, comprising:
positioning a guide tube, for assisting in disposing an anchoring base within the patient's skull, through a portal in a patient's scalp, the guide tube formed to have an inner guide tube wall defining a lumen extending longitudinally through the guide tube and sized to allow passage of the anchoring base and for guiding the anchoring base to an anchoring location on the patient's skull, the guide tube further extending from a first terminal end to a second terminal end, wherein at least a portion of the outer surface defines a beveled distal tip operable to engage the patient's scalp to position the scalp a distance from an inner wall surface of the guide tube, and a flange extending outwardly from the outer surface at a distance from the beveled distal tip that is selected such that the flange stabilizes a portion of the patient's scalp near a portal in the patient's scalp when the beveled distal tip of the guide tube is pressed into a portion of the portal in the patient's scalp when the first terminal end engages the patient's skull;
contacting the patient's skull with the first terminal end of the guide tube;
stabilizing the patient's scalp with the flange;
engaging the anchoring base with an anchoring base insertion tool having an engaging portion to engage the anchoring base receptacle and a shaft coupled to and extending from the engaging portion, including deforming a deformable distal portion of the engaging portion by contacting the deformable distal portion to the anchoring base receptacle and holding the anchoring base to the anchoring base insertion tool with the deformed deformable distal portion;
passing the anchoring base through the guide tube once the scalp is stabilized;
inserting the anchoring base into the patient's skull such that a top surface is at least level with or below an outer surface of the patient's skull, the anchoring base having an exterior surface extending from a top surface end to a second end and sized and shaped to be implanted within in a patient's skull, the anchoring base including an externally threaded outer portion including a thread extending from the top surface end to the second end of the anchoring base; a tool engaging portion; a distal tip, and an anchoring base receptacle extending from the top surface of the anchoring base defining a bore within the anchoring base;
providing a locatable fiducial marker, including a shaft extending from the fiducial marker, the shaft having a distal shaft portion that is sized and shaped to be received and engaged into the base receptacle, the shaft being sized and configured to separate the fiducial marker from the base by a first distance when the fiducial marker shaft is engaged into the anchoring base receptacle;
providing a registration receptacle, separate from and interchangeable with the fiducial marker into the base receptacle, the registration receptacle having a shaft extending from the registration receptacle, the shaft having a distal shaft portion sized and shaped to be received and engaged into the anchoring base receptacle when the fiducial marker shaft is not engaged into the base receptacle, the shaft being sized and configured to separate the registration receptacle from the base by the first distance when the registration receptacle shaft is engaged into the anchoring base receptacle; and
providing a plug to be positioned in the anchoring base receptacle when both the fiducial marker shaft and the registration receptacle shaft are not engaged to the anchoring base receptacle.

24. The method of claim 23, further comprising:
passing a trocar through the guide tube;
forming the portal in the scalp with the trocar once it is passed through the guide tube; and
removing the trocar from the guide tube;
wherein passing the anchoring base through the guide tube occurs after the trocar is removed.

25. The method of claim 23, further comprising: selectively engaging one of the locatable fiducial marker, the registration receptacle and the plug with the anchoring base.

* * * * *